Aug. 4, 1959 M. ROBICHON Plant Pat. 1,857
ROSE PLANT
Filed Dec. 10, 1958
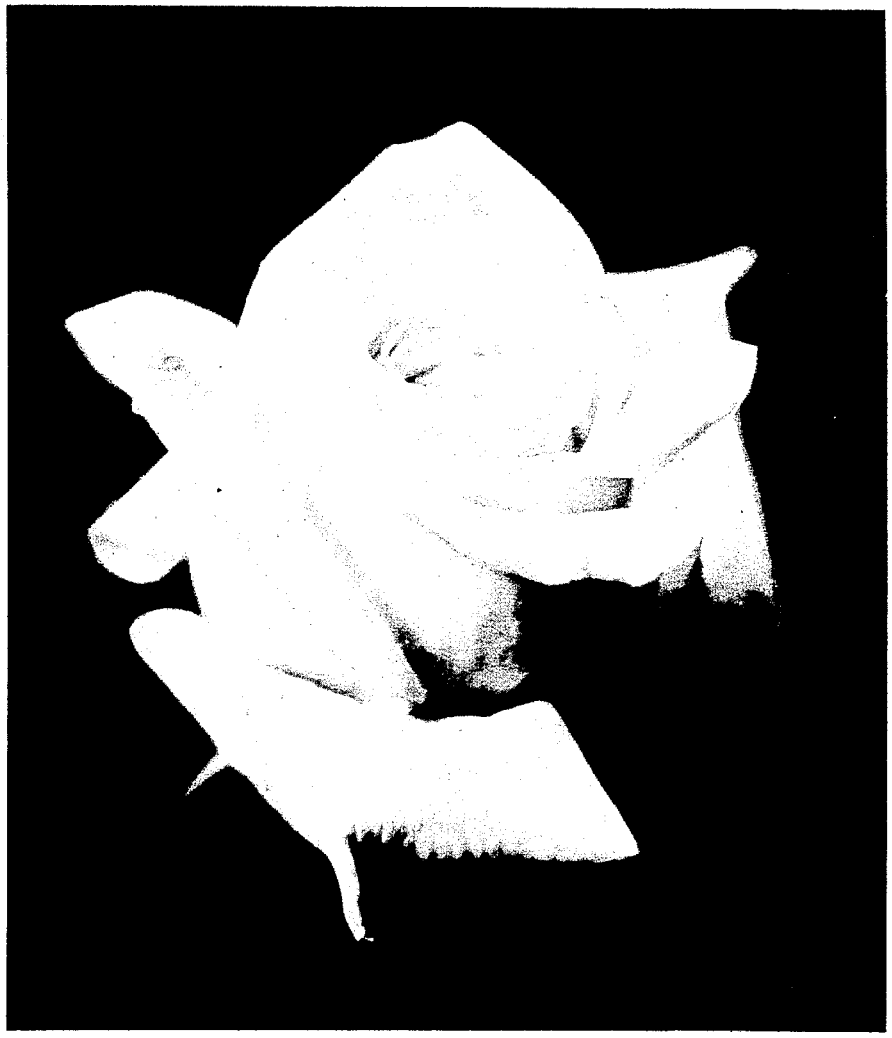
Inventor.
Marcel Robichon
By: Robb & Robb
Attorneys.

United States Patent Office

Plant Pat. 1,857
Patented Aug. 4, 1959

1,857

ROSE PLANT

Marcel Robichon, Pithiviers, Loiret, France, assignor to Ilgenfritz Nurseries, Inc., Monroe, Mich., a corporation of Michigan Application December 10, 1958, Serial No. 779,511

1 Claim. (Cl. 47—61)

The present invention relates to a new and distinct variety of rose plant of the hybrid tea class, which was originated by me by crossing the variety "Ophelia" (unpatented) with the variety "Catherine Kordes" (unpatented).

As the result of this breeding, I have produced a new variety of rose plant which is distinct from its parents, as well as from all other varieties of its class of which I am aware, and which is particularly characterized as to novelty by the unique combination of the following features:

(1) A strong habit of plant growth;

(2) Full form and strong tea fragrance of the blooms; and (3) A distinctive tinting of the white general color tonality of the blooms, with the tips of the flower petals having a delicate tint of pink and creating an overall appearance of delicate pink color, particularly in the center of the flower.

Asexual reproduction of my new variety by budding, as performed in France, and also at Monroe, Michigan, U.S.A., shows that the foregoing characteristics and distinctions come true to form and are established and transmitted through succeeding propagations.

The accompanying drawing shows a typical flower specimen of my new variety as depicted in color as nearly true as it is reasonably possible to make the same in a color illustration of this character.

The following is a detailed description of my new variety, with color terminology in accordance with The Horticultural Colour Chart issued by the British Colour Council in collaboration with The Royal Horticultural Society, except where general color terms of ordinary dictionary significance are obvious:

Type: Hardy; half-dwarf; bush; outdoor; seedling; for cut flowers and for garden decoration.
Class: Hybrid tea.
Breeding: Seedling.
*Seed parent.*—"Ophelia."
*Polylen parent.*—"Catherine Kordes."
Propagation: Hold its distinguishing characteristics through succeeding propagations by budding.

*Flower*

Locality where grown and observed: Monroe, Michigan, U.S.A.
Continuity: Continuous.
Fragrance: Strong. Nature—tea.
Flowers borne: Singly; on strong, long stems.
Quantity of bloom: Free, outdoors.
Bud:
*Peduncle.*—Medium length; medium caliper; erect; stiff; smooth. Color—green-bronze.
*Before calyx breaks.*—Size—large. Form—short; with foliaceous appendages on the surface of the bud; with stout foliaceous parts extending beyond the tip of the bud equal to ¼ or more of its length. Color—Spinach Green, Plate 0960/1.
*As calyx breaks.*—Color—Uranium Green, Plate 63/2.
*As first petal opens.*—Size—large. Form—ovoid. Color: outside—white, shading to Sap Green, Plate 62/2 at base, with tip of petal Nasturtium Red, Plate 14/3; inside—white, shading to Sap Green, Plate 62/2 at base, and tipped with Apricot, Plate 609/3.
Bloom:
*Size (when fully open).*—From 4 inches to 5 inches.
*Petalage.*—Very double; arranged regularly. Number of petals under normal conditions—from 60 to 65.
*Form.*—Full and high-centered at first, and remaining high-centered; petals being at first tightly rolled outward, and remaining tightly rolled outward at maturity.
Petals:
*Texture.*—Thick.
*Appearance.*—Inside—satiny. Outside—satiny.
*Shape.*—Outside—oval, with 3 notches. Intermediate—oval. Inside—oval.

This description of a newly opened flower was made from a rose grown outdoors in the month of June at Monroe, Michigan, U.S.A.:

*Color.*—Outer petal: outside surface—white, shading to Sap Green, Plate 62/2 at base, and tipped with Rose Opal, Plate 022/3; inside surface—white, shading to Sap Green, Plate 62/2 at base, and tipped with Sap Green, Plate 62/2, edged with Chinese Coral, Plate 614/2. Intermediate petal: outside surface—white, shading to Sap Green, Plate 62/2 at base, and tipped with Rose Opal, Plate 022/3; inside surface—white, shading to Sap Green, Plate 62/2 at base, and tipped with Sap Green, Plate 62/2, edged with Chinese Coral, Plate 614/3. Inner petal: outside surface—white, edged with Rose Bengal, Plate 25/3, and shading to Sap Green, Plate 62/3; inside surface—white, edged with Rose Bengal, Plate 25/3, and shading to Sap Green, Plate 62/3.

This description was made from a rose that was open for 3 days outdoors in the month of June, at Monroe, Michigan, U.S.A.:

*Color.*—Outer petal: outside surface—white, shading to Sap Green, Plate 62/2 at base, and tipped with Rose Opal, Plate 022/3; inside surface—white, edged with Rose Bengal, Plate 25/3, and shading to Sap Green, Plate 62/3. Inner petal: outside surface—white, edged with Rose Bengal, Plate 25/3, and shading to Sap Green, Plate 62/3; inside surface—white, edged with Rose Bengal, Plate 25/3, and shading to Sap Green, Plate 62/3.
*General color effect.*—Newly opened flower—white, with slight suffusion of Carmine Rose, Plate 621/3. 3-days open—white, with slight suffusion of Carmine Rose, Plate 621/3.
*Behavior.*—Drop off cleanly; is not affected by cold, hot, wet or dry weather.
*Flower longevity.*—On bush in garden—5 days in June. Cut roses grown outdoors and kept at living-room temperatures—6 days in June.

*Reproductive organs*

Stamens: Very few; arranged irregularly; mixed with petaloids. Color—white and yellow.
Filaments: Medium length; most with anthers. Color—reddish.

Anthers: Large; all open at once. Color—yellow.
Pollen: Abundant. Color—gold.
Pistils: Many.
Styles: Very uneven; medium length; thin; loosely separated.
Stigma: Color—white.
Ovaries: All enclosed in calyx.
Hips: Very short; pointed; very smooth; walls thick and fleshy. Color—green.
Sepals: Permanent; spear-shaped. Color—green-gray.
Seeds: Many; medium size.

*Plant*

Foliage:

*Leaves.*—Compound of 5 leaflets; normal abundance; medium large; heavy; leathery.

*Leaflets.*—Shape—oval, with apex obtuse. Base—round. Margin—simply serrate.

*Color.*—Mature: upper surface—dark green; under surface—grey-red. Young: upper surface—normal green; under surface—grey-red.

*Rachis (the supporting stem of the compound leaf).*—Medium caliper. Upper side—grooved. Under side—smooth.

*Stipules.*—Medium length; medium width; with points of medium length turning out at an angle of less than 45°.

*Disease resistance.*—Resistant to mildew and blackspot, as evidenced by comparison with other varieties grown under comparable cultural conditions at Monroe, Michigan, U.S.A.

Growth:

*Habit.*—Upright; branched.

*Growth.*—Vigorous.

*Canes.*—Medium caliper.

*Main stems.*—Color—bronze. Thorns—few; long; with long, narrow base. Prickles—none. Hairs—none.

*Branches.*—Color—dull bronze. Thorns—few; medium length; straight; with long, narrow base. Prickles—none. Hairs—none.

*New shoots.*—Color—dull bronze. Thorns—few; hooked downward; with narrow base. Prickles—none. Hairs—none.

I claim:

A new and distinct variety of rose plant of the hybrid tea class, substantially as herein shown and described, characterized particularly as to novelty by the unique combination of a strong habit of plant growth, full form and strong tea fragrance of the blooms, and a distinctive tinting of the white general color tonality of the blooms, with the tips of the petals having a delicate tint of pink, creating an overall appearance of delicate pink color, particularly in the center of the flower.

No references cited.